(12) United States Patent
Latronica

(10) Patent No.: US 9,005,090 B2
(45) Date of Patent: Apr. 14, 2015

(54) FULL BODY EXERCISE BAND SYSTEM

(71) Applicant: Yoga Bent, LLC, Highland Park, IL (US)

(72) Inventor: Miguel James Latronica, Riverwoods, IL (US)

(73) Assignee: Yoga Bent, LLC, Riverwoods, IL (US)

(*) Notice: Subject to any disclaimer, the term of this patent is extended or adjusted under 35 U.S.C. 154(b) by 0 days.

(21) Appl. No.: 14/085,386

(22) Filed: Nov. 20, 2013

(65) Prior Publication Data

US 2014/0155233 A1 Jun. 5, 2014

Related U.S. Application Data

(63) Continuation of application No. PCT/US2012/038893, filed on May 21, 2012, and a continuation-in-part of application No. 13/601,524, filed on Aug. 31, 2012, now Pat. No. 8,608,629, which is a continuation of application No. 12/463,368, filed on May 8, 2009, now Pat. No. 8,282,536.

(60) Provisional application No. 61/488,638, filed on May 20, 2011.

(51) Int. Cl.
| | |
|---|---|
| A63B 21/00 | (2006.01) |
| D04G 5/00 | (2006.01) |
| A63B 21/04 | (2006.01) |
| A63B 21/055 | (2006.01) |
| A63B 23/02 | (2006.01) |
| A63B 23/035 | (2006.01) |
| A63B 23/12 | (2006.01) |
| A63B 26/00 | (2006.01) |
| A63B 21/16 | (2006.01) |
| A63B 23/00 | (2006.01) |

(52) U.S. Cl.
CPC ......... *A63B 21/1465* (2013.01); *A63B 21/1645* (2013.01); *A61L 2430/04* (2013.01); *D04G 5/00* (2013.01); *A63B 21/0442* (2013.01); *A63B 21/0555* (2013.01); *A63B 21/0557* (2013.01); *A63B 21/1419* (2013.01); *A63B 21/1423* (2013.01); *A63B 21/1484* (2013.01); *A63B 23/0238* (2013.01); *A63B 23/03541* (2013.01); *A63B 23/1245* (2013.01); *A63B 23/1272* (2013.01); *A63B 26/003* (2013.01);
(Continued)

(58) Field of Classification Search
CPC ............. A63B 22/001; A63B 22/0664; A63B 21/225; A63B 22/0015; A63B 21/0053; A63B 2022/0676; A63B 2022/067; A63B 21/0051; A63B 2022/002; A63B 22/0023; A63B 22/203; A63B 21/012; A63B 2022/0682; A63B 21/0058; A63B 21/0088
USPC ........................... 482/91, 121–129, 139, 134
See application file for complete search history.

(56) References Cited

U.S. PATENT DOCUMENTS

| 4,667,624 A * | 5/1987 | Smith ........................... 119/770 |
| 5,921,903 A * | 7/1999 | Lawrence ..................... 482/140 |

(Continued)

*Primary Examiner* — Stephen Crow
(74) *Attorney, Agent, or Firm* — Enrique Perez; Rosenbaum IP, P.C.

(57) ABSTRACT

A system for performing proprioceptive neuromuscular facilitation ("PNF") stretching. The system includes a harness portion comprising a harness strap with movably attached buckle portions and a hook receptacle surrounding the harness strap to support the harness strap when the hook receptacle is suspended. The harness strap includes a mini-strap with buckle portions extending in parallel with the harness strap. The harness strap buckle portions mate with the mini-strap buckle portions to form a double loop harness configuration, and alternatively, combine with a single loop enabler to form a single loop harness configuration. An attachment strap is configured for attachment to a fixing structure by a movably attached hooking mechanism, which varies the distance between the attaching end of the attachment strap and the hooking mechanism. The harness portion attaches to the attachment strap attached to the fixing structure to provide a user with a body support while in un-balanced positions.

16 Claims, 16 Drawing Sheets

(52) U.S. Cl.
CPC ....... *A63B2023/006* (2013.01); *A63B 2210/50* (2013.01); *A63B 21/00065* (2013.01)

(56) References Cited

U.S. PATENT DOCUMENTS

| | | | |
|---|---|---|---|
| 6,036,625 A * | 3/2000 | Woodruff | 482/121 |
| 6,047,665 A * | 4/2000 | Deveaux | 119/770 |
| 6,726,606 B2 * | 4/2004 | Jacobsen | 482/121 |
| 6,921,354 B1 * | 7/2005 | Shifferaw | 482/91 |
| 7,261,679 B2 * | 8/2007 | Sload | 482/124 |
| 7,284,504 B1 * | 10/2007 | Purschwitz et al. | 119/792 |
| 7,481,747 B2 * | 1/2009 | Lechleiter | 482/57 |
| 8,002,681 B2 * | 8/2011 | Kopp | 482/124 |
| 2006/0249097 A1 * | 11/2006 | Goldberg | 119/771 |
| 2012/0053026 A1 * | 3/2012 | Kopp | 482/124 |

* cited by examiner

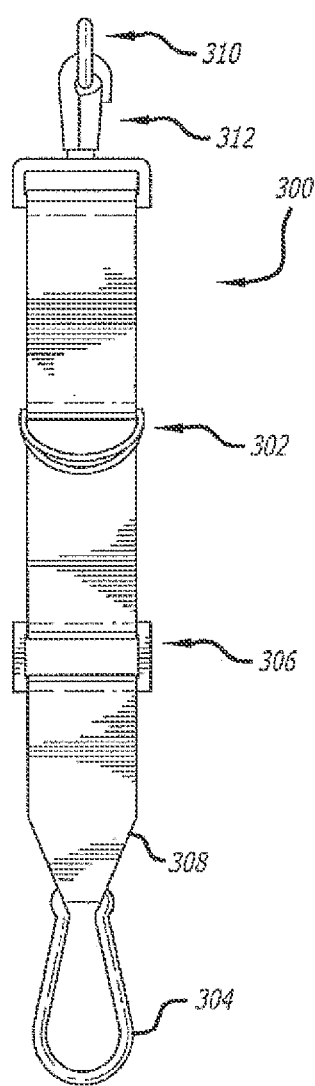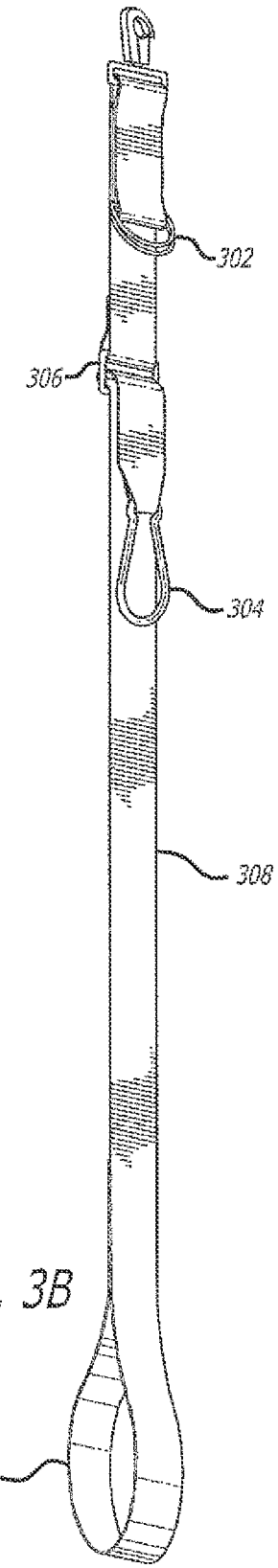
FIG. 3A
FIG. 3B

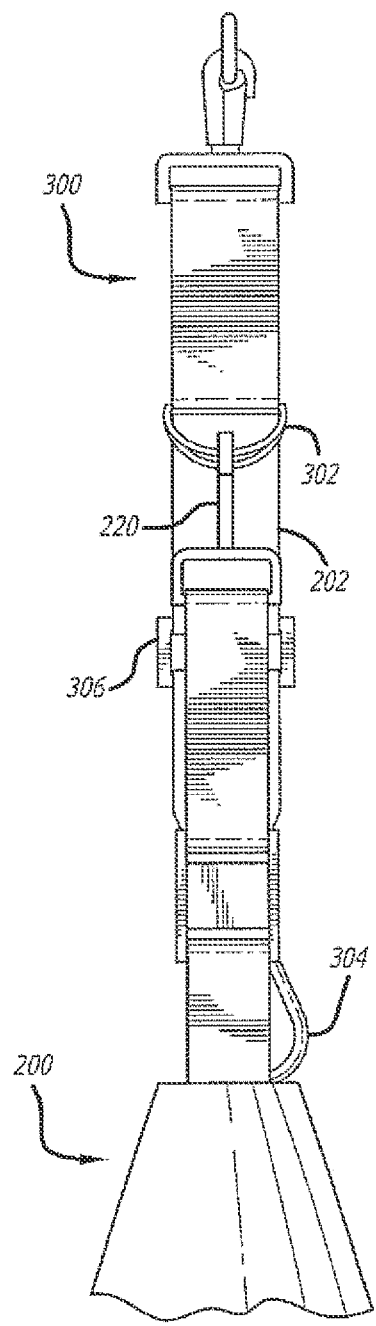
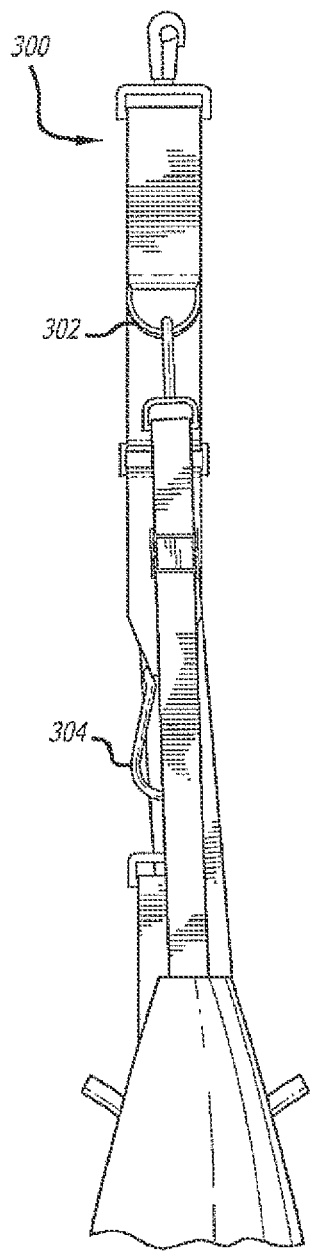
FIG. 3C
FIG. 3D

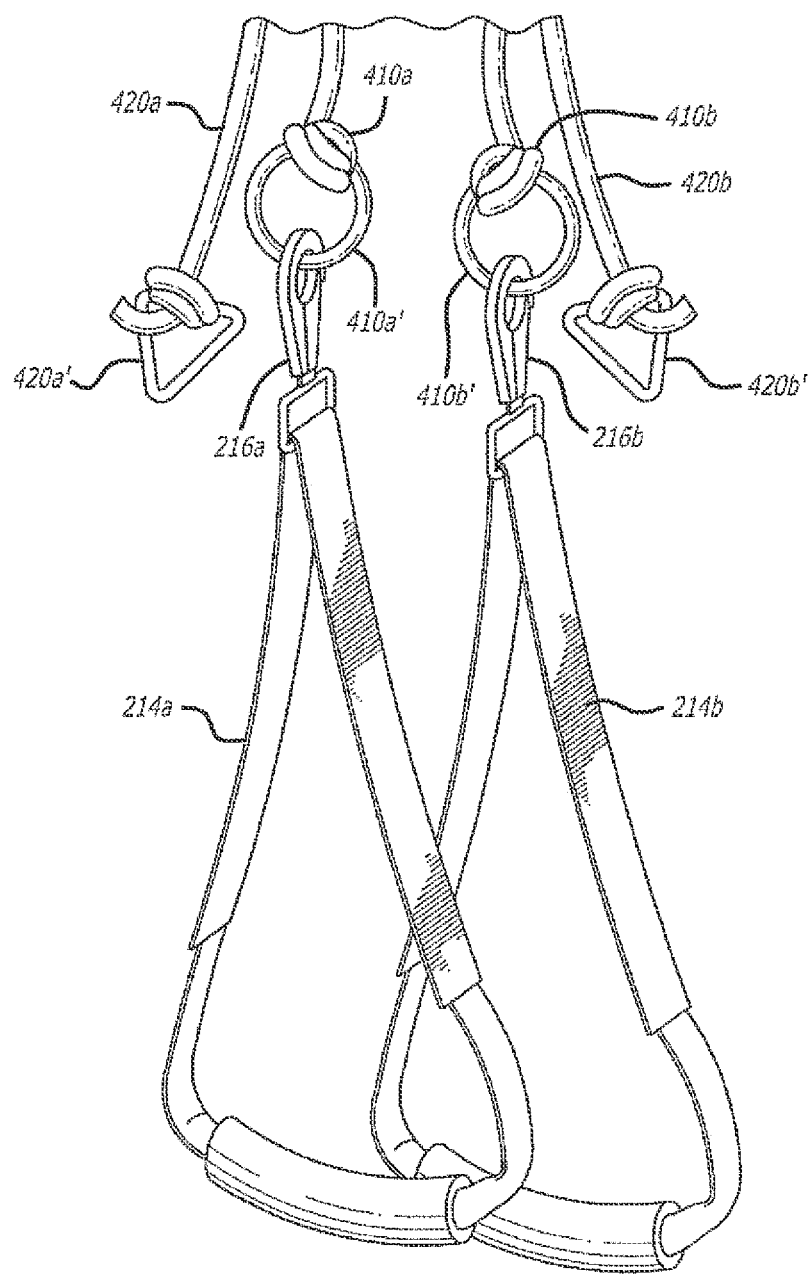

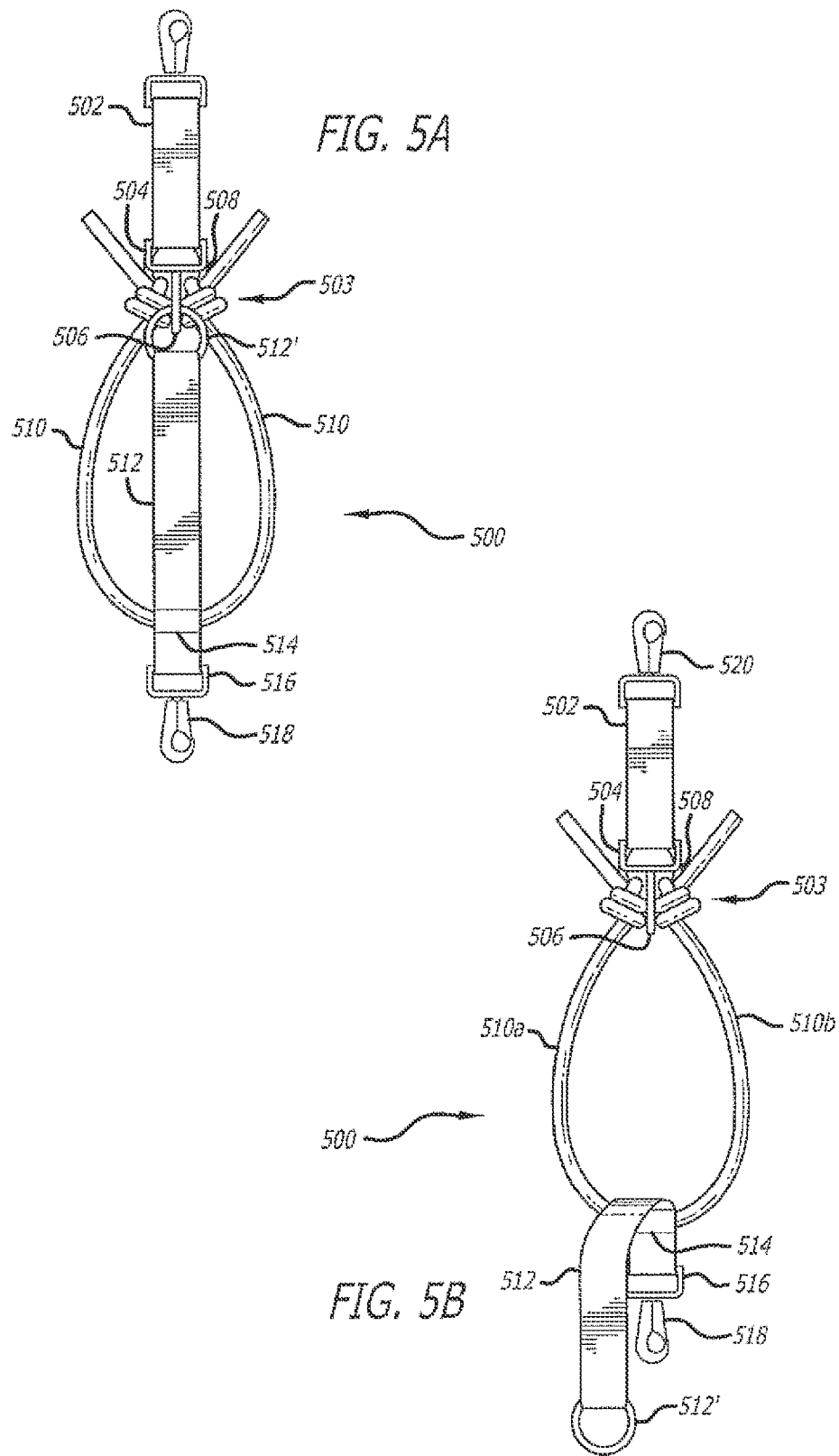

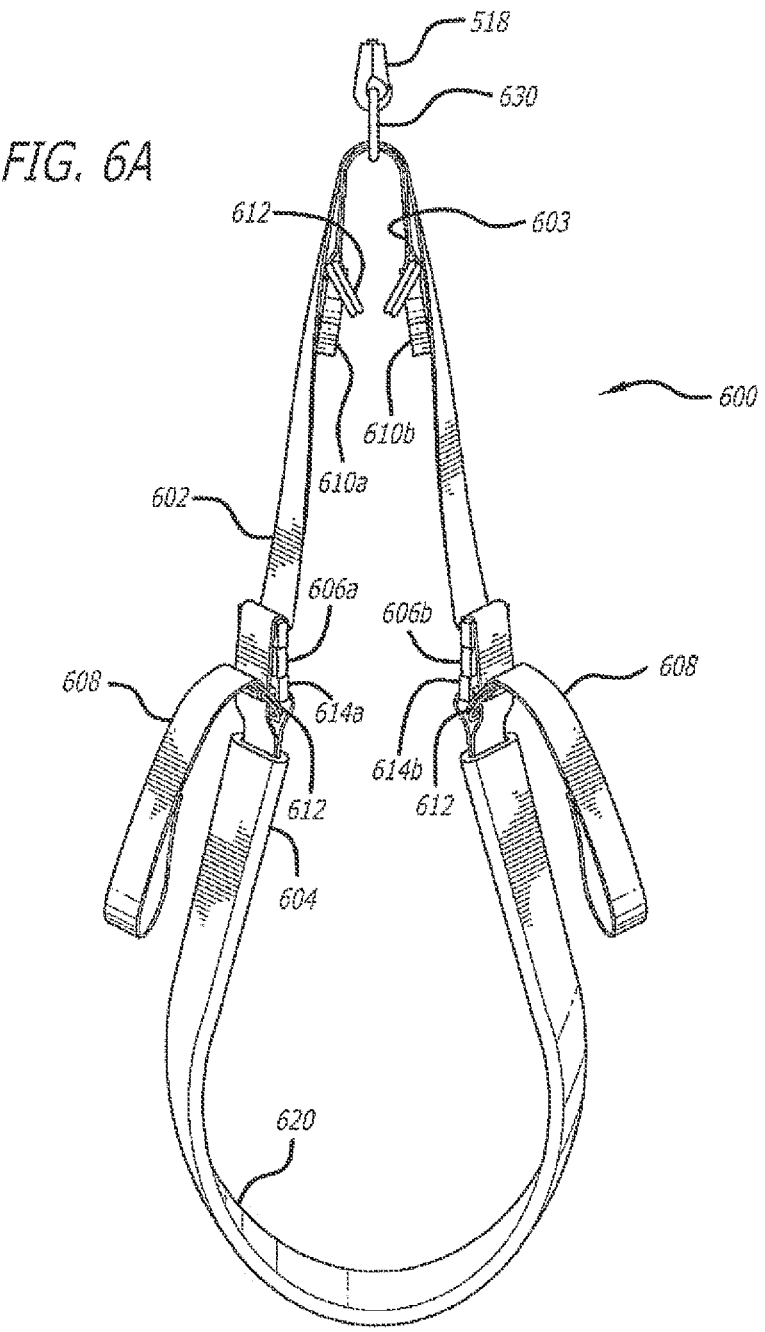

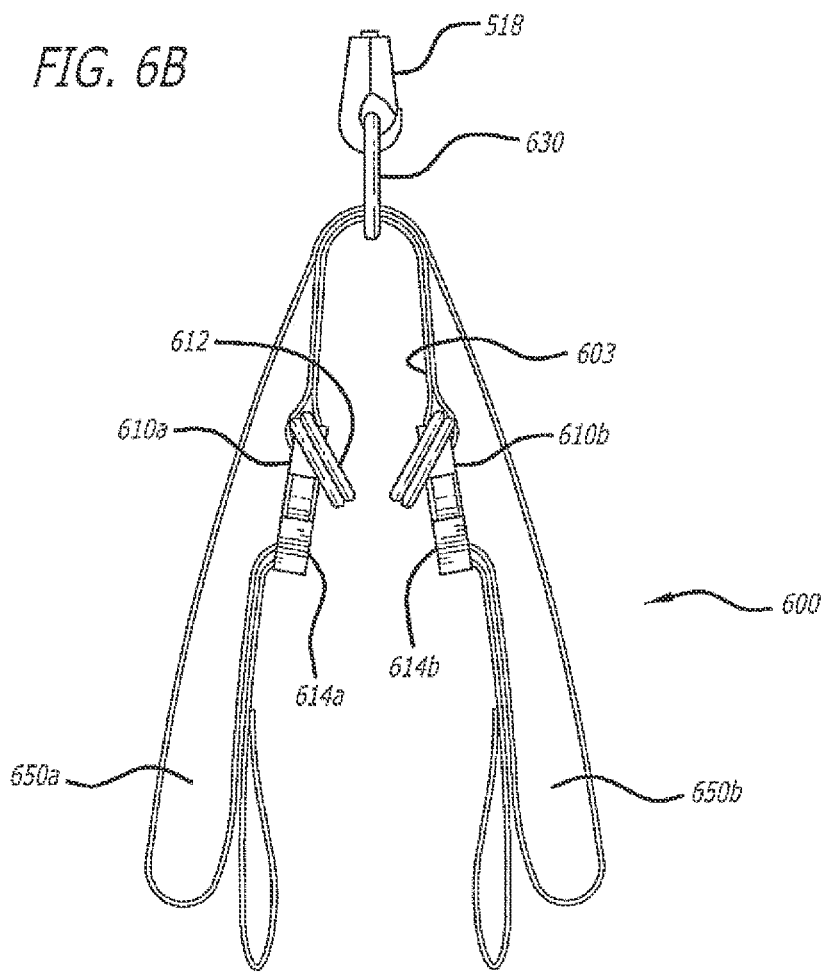

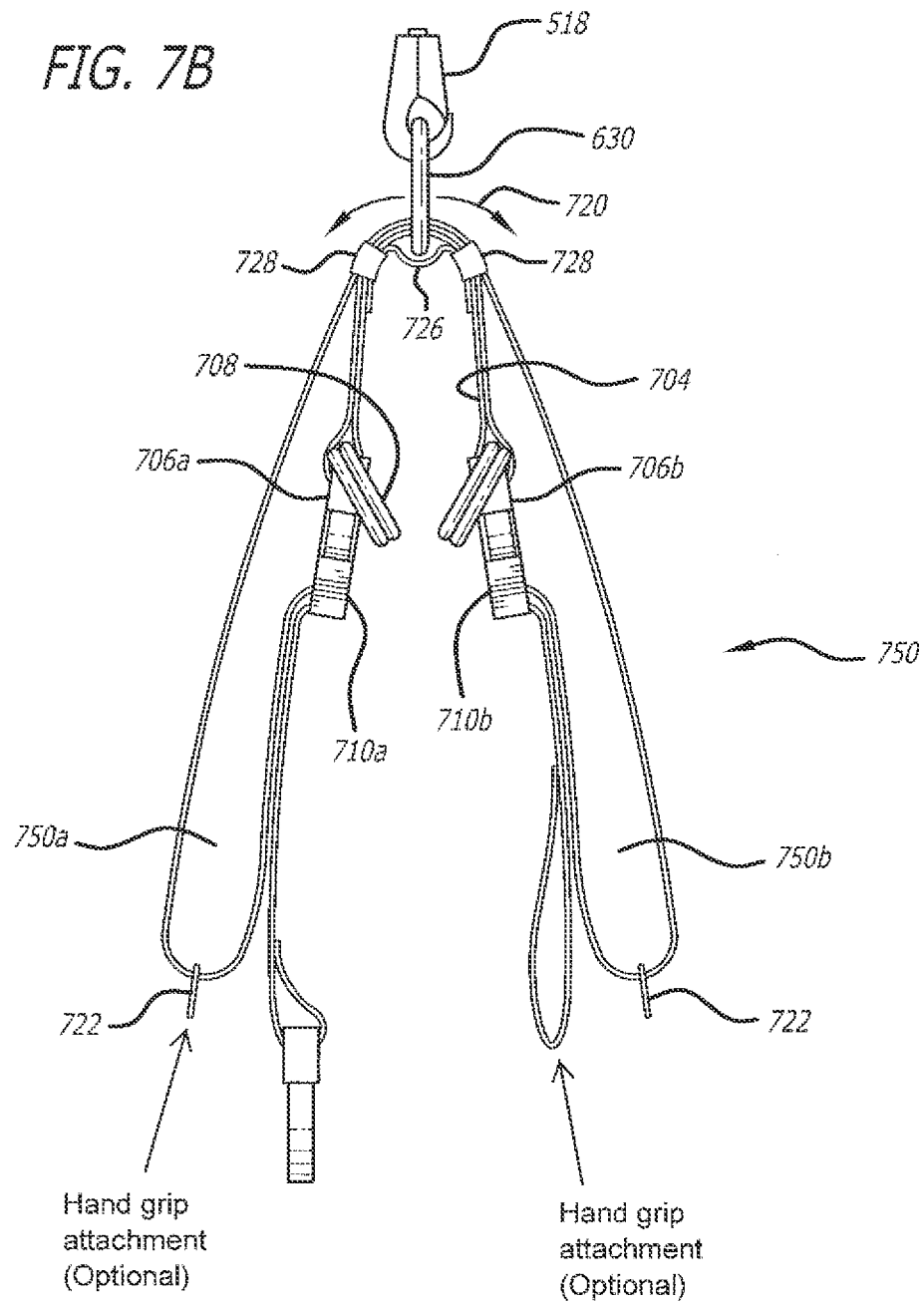

FULL BODY EXERCISE BAND SYSTEM

CROSS-REFERENCES TO RELATED APPLICATIONS

The present application is a continuation and claims priority under 35 U.S.C. §120 and §365(c) to PCT Patent Application Serial No. PCT/US2012/038893, filed on May 21, 2012, the contents of which are incorporated by reference herein in its entirety. PCT Application Serial No. PCT/US2012/038893 claims priority to U.S. Provisional Application Ser. No. 61/488,638, filed on May 20, 2011, the contents of which are incorporated by reference herein in its entirety. This application also claims priority as a continuation-in-part application to currently co-pending U.S. patent application Ser. No. 13/601,524, filed on Aug. 31, 2012, the contents of which are incorporated by reference herein in its entirety. U.S. patent application Ser. No. 13/601,524 claims priority as a continuation of U.S. patent application Ser. No. 12/463,368, filed on May 8, 2009, now U.S. Pat. No. 8,282,536, the contents of which are incorporated by reference herein in its entirety.

BACKGROUND OF THE INVENTION

1. Field of the Invention

The present invention relates to an apparatus that enables therapeutic exercise, and more particularly, to a therapeutic body strap configured to enable the exercise of selected body parts.

2. Description of Related Art

Exercise equipment has long addressed basic fitness objectives, such as for example, increasing muscle strength, improving cardiovascular functioning, and improving flexibility. The basic objectives have typically been addressed using basic equipment types. Increasing muscular strength has been addressed by resistance training using weights, elastic bands or other devices that challenge muscle motion with resistance. A variety of apparatuses and props are used for cardiovascular training in aerobics routines; and some types of equipment, such as exercise bikes and treadmills may be found in spin classes, and other group exercise approaches. Flexibility, a fitness objective typically minimized in favor of strength and cardio, is usually addressed by incorporating stretching, either as a warm-up, or a cool-down. Fitness experts tend to promote fitness programs that address all three basic objectives. However, addressing all three objectives typically requires a time commitment that not many are able to make. In addition, until recently, home exercise equipment had not evolved to the point where a fitness program that targeted all three objectives could be cost-effective for many fitness enthusiasts. Yoga focused on stretching and flexibility, but has not been favored for developing strength and cardio by typical fitness enthusiasts.

Modern exercise disciplines have taken a more integrative approach that promotes all three fitness objectives. Resistance training programs are now often designed to provide substantial cardio benefits along with increases in strength. In addition, core strength has evolved as an important fitness objective. Pilates, yoga, and personal fitness trainers as well as an increasingly fitness-educated gym membership have worked to substantially change the look of gyms and the variety of programs used by an increasingly fitness-conscious public. Resistance training and cardio, and the equipment traditionally used for strength and cardio, are still important components of modern fitness programs. Their use has been adapted to incorporate modern concepts that help to streamline fitness programs making them more efficient and better adapted to assist fitness trainees with every day, functional body motions and work. Resistance training has been adapted to include body de-stabilization, which may include, for example, performing basic weight-lifting motions such as a shoulder press while seated on an inflated exercise ball; or while standing on a soft compressible hemisphere. Props and apparatuses such as large rubber bands, large weighted nylon tubes, weighted balls (medicine balls), and other devices are now staples of gym equipment taking their place next to squat racks, benches, weightlifting machines, aerobics studios and spin studios.

Modern exercise disciplines have not placed any more emphasis on flexibility, addressing it largely as a natural consequence of the more integrated approach to fitness. Stretching still remains largely an afterthought except by yoga, which has increased in popularity as fitness enthusiasts are discovering that yoga can be used to increase strength and even cardiovascular fitness. One problem encountered with stretching is that it is typically done by static stretching in an exaggerated manner. Static stretching involves stretching a muscle or muscle group against a static force such as gravity or a fixed support. An example of static stretching involves straightening a leg and bending over the leg to stretch the hamstring while keeping the leg straight and immobile. Such stretches are often made more intense by increasing the force on the muscle, such as by pulling on the foot to deepen the bend and force the hamstring into a deeper stretch. Static stretching is often exaggerated and may lead to injury. Many believe that a deeper and more intense stretch is better but end up stretching the muscle to the point where it tears. Even if the muscle does not tear, the deep, forced stretch may leave a muscle weaker and unable to flex as quickly or as forcefully as before.

An alternative to passive stretching is active stretching, which is based on reciprocal inhibition. When a muscle contracts, other muscles are stretched. For example, the triceps are stretched when the biceps are flexed. While an alternative to passive stretching, active stretching may not help lengthen muscle fibers sufficiently to provide as much benefit as passive stretching.

Yoga involves both passive and active stretching. In addition, yoga has evolved to include elements that focus more on strength and to some extent, even cardio providing a comprehensive fitness. One problem with yoga is that it involves poses that remain too difficult for too many seeking the benefits it offers. In addition, the basic poses often require a balance and flexibility that many lack the patience to work into over a period of time.

Modern fitness disciplines are providing increased benefits for their proponents. However, even modern disciplines continue to create a substantial risk of injury. Many factors contribute to the risk of injury. Fitness disciplines have become more integrated, but often fail to address all possible ranges of motion or the interaction of muscle groups when in motion. Exercises tend to be linear in that the focus is on larger muscles involved in basic motions such as pushing and pulling by the arms, or pushing by the legs. In addition, people tend to begin a fitness program without carefully assessing their strengths and weaknesses, or focus too much on one facet of their physique (e.g. chest over back muscles). An imbalanced body becomes stronger in the areas of imbalance and often ends up injured. The end result is that the fitness program is stopped while recovering from injury since most disciplines are not therapeutic.

One form of stretching, called proprioceptive neuromuscular facilitation ("PNF") stretching, has been used in therapeutic applications and more recently by healthy athletes for sport specific training PNF stretching combines isometric contractions with passive stretching to encourage flexibility and coordination throughout the entire range of motion of a limb. PNF techniques include Hold Relax, Contract-Relax with Agonist Contract (CRAC), Hold-Relax-Swing/Hold-Relax Bounce, Rhythmic Initiation, and Rhythmic Stabilization. The techniques are typically performed with the assistance of a therapist who provides resistance and cues for flexing, relaxing and stretching according to the exercise protocol. PNF stretching is not a simple form of stretching. In order to perform PNF stretching properly, the guidance of a therapist is typically employed. There is also a need for exercise equipment that operates consistently with the principles of PNF stretching.

In view of the above, there is a need for an exercise system that strengthens and stretches muscles in a manner that promotes balanced conditioning, comprehensive conditioning of large and small muscles involved in the complete range of linear and rotational motion of all body parts, and stretching based on PNF stretching principles. An exercise system is also needed to train a user in basic yoga poses by enhancing the user's balance and flexibility. An exercise system is also needed that provides total body conditioning in a home environment without the need for expensive, large and heavy equipment.

SUMMARY

In view of the above, a body band system is provided for performing stretching, in particular, proprioceptive neuromuscular facilitation ("PNF") stretching, while enabling the user to position the body in un-balanced positions. The body band system includes a harness portion comprising a harness strap, and a hook receptacle configured to surround the harness strap to support the harness strap when the hook receptacle is suspended. The harness strap includes a mini-strap shorter than the harness strap. The mini-strap extends in parallel with the harness strap in a center harness strap portion. A hook receptacle encloses the mini-strap with the harness strap. The mini-strap includes first and second mini-strap buckle portions attached to each end of the mini-strap. First and second harness strap buckle portions are movably attached on opposite extensions of the harness strap extending from the center harness strap portion. The first and second harness strap buckle portions are configured to mate with the first and second mini-strap buckle portions to form a double loop harness configuration, and to combine with a single loop enabler to form a single loop harness configuration. An attachment strap is configured for attachment to a fixing structure at one end. The attachment strap includes a movably attached hooking mechanism to vary the distance between the attaching end of the attachment strap and the hooking mechanism. The harness portion is configured for attachment to the attachment strap attached to the fixing structure to provide a user with a body support while in un-balanced positions.

Various advantages, aspects and novel features of the present invention, as well as details of an illustrated embodiment thereof, will be more fully understood from the following description and drawings.

Other systems, methods and features of the invention will be or will become apparent to one with skill in the art upon examination of the following figures and detailed description.

It is intended that all such additional systems, methods, features and advantages be included within this description, be within the scope of the invention, and be protected by the accompanying claims.

BRIEF DESCRIPTION OF THE DRAWINGS

The description of examples of the invention below can be better understood with reference to the following figures. The components in the figures are not necessarily to scale, emphasis instead being placed upon illustrating the principles of the invention. In the figures, like reference numerals designate corresponding parts throughout the different views.

FIGS. 3A-3D depict an example attachment strap that may be used in examples of a body band system.

FIGS. 4A-4F depict an example of a dual-loop band device that may be used in examples of a body band system.

FIGS. 5A and 5B depict an example of a tension converter that may be used in examples of a body band system.

FIGS. 6A and 6B depict an example of a harness device that may be used in examples of a body band system.

FIGS. 7A and 7B depict another example of a harness device that may be used in another example implementation of a body band system.

DETAILED DESCRIPTION

In the following description of example implementations, reference is made to the accompanying drawings that form a part hereof, and which show, by way of illustration, example implementations of the invention. Other examples may be utilized and structural changes may be made without departing from the scope of the invention.

I. The Body Band System

The body band system described with reference to the example implementations illustrated in the attached figures may be used as an exercise apparatus to achieve or maintain a desired level of physical fitness, or as a therapeutic device to aid in the recovery from injury. The body band system may be used for increasing strength in muscles targeted by specific exercises while activating stabilizing and supporting muscles. Muscles may also be stretched using proprioceptive neuromuscular facilitation ("PNF") stretching. The body band system may also be used as an aid in the practice of yoga by providing support, resistance, and destabilization in targeted areas of the user's body as the user attempts various poses.

As described in more detail below with reference to the drawings, the body band system includes an attachment device and at least one body band apparatus. The attachment device includes a body band fixing mechanism for attaching the body band to a solid stationary support such as a wall, and at least one attachment mechanism for attaching at least one body band apparatus. The at least one body band apparatus may include an upper body band apparatus and/or lower body band apparatus. The upper body band apparatus may include a dual-loop device. The lower body band apparatus may include a tension converter, and a harness portion. These components of the body band system are described generally with reference to examples of uses of the body band in FIGS. 1A-1E, and in more detail in FIGS. 2A-6B.

Figure 1A:
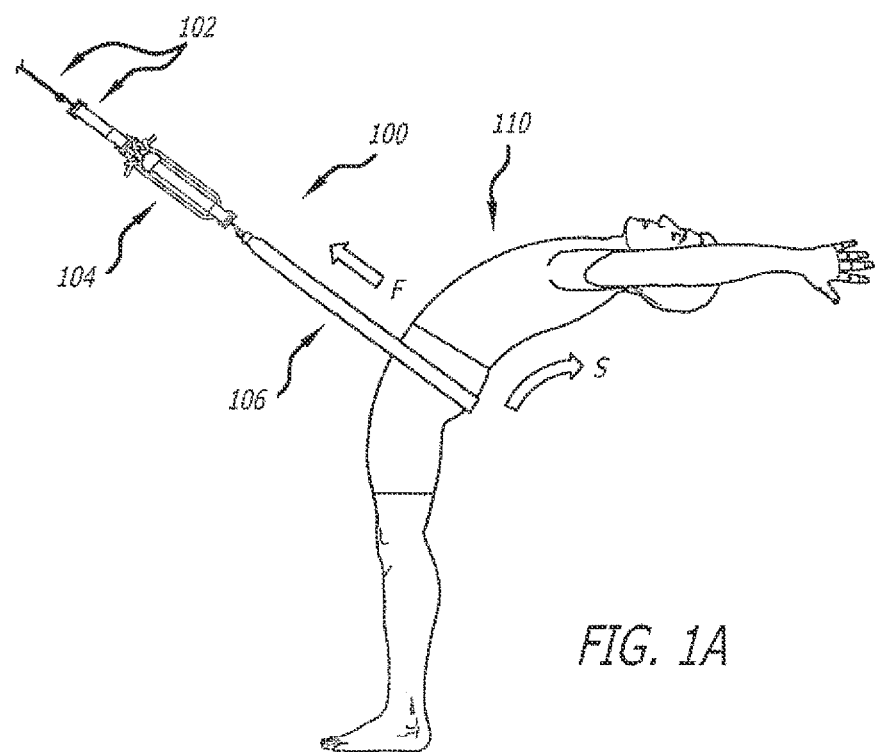
FIGS. 1A-1E illustrate applications of an example body band.

FIGS. 1A-1E illustrate examples of applications of an example body band 100. Referring to FIG. 1A, the body band 100 includes an attachment strap 102 and a body band apparatus, which in FIG. 1A includes a tension converter 104, and a harness portion 106. The attachment strap 102 is an attachment device for the body band 100 providing a body band fixing mechanism for attaching the body band 100 to a wall or to a suitable structure that provides a fixed position capable of withstanding forces generated on the body band. The tension converter 104 provides a dual-tension band to permit selection between a low elasticity and a high elasticity. The harness portion 106 includes a body support for supporting the user during an exercise.

The body band 100 in FIG. 1A is shown in use by a user 110 performing a back bend. The body band 100 provides a supporting force F aligned with the body band 100. The supporting force may be applied using a low elastic setting on the dual-tension band of the tension converter 104 or a high elastic setting on the dual-tension band of the tension converter 104. The user may rely on the support provided by the body band 100 to lean backwards in a position that would otherwise create a sense of vulnerability. The support allows the user to gradually overcome any fear in settling into the back bend. The supporting force F also provides a fixed position for stretching the user's back muscles along stretch direction S. The user may adjust the angle of the supporting force F and stretch direction S relative to the floor by adjusting the length of the body band 100 as described in more detail below with reference to the figures below. The user may also select between a low, or substantially no, elasticity, and a higher elasticity setting using the dual-tension band of the tension converter 104. By selecting the higher elasticity setting, the user 110 may add a sense of instability that induces supporting muscles to engage. The sense of instability created by the higher elasticity setting may also provide the user 110 with a more gradual transition to the fully extended back bend. This gradual transition may train the user's neuromuscular and neurological system to adjust to the fully extended pose by lessening the sense of vulnerability that the pose may induce. The user 110 may begin using the low elasticity setting and gradually move to the higher elasticity setting. The user's training in the back bend provides the user with the benefits of stretching, including PNF stretching, and trains the user's muscles to more easily enter yoga poses requiring a deep backwards bend and balance.

Figure 1B:
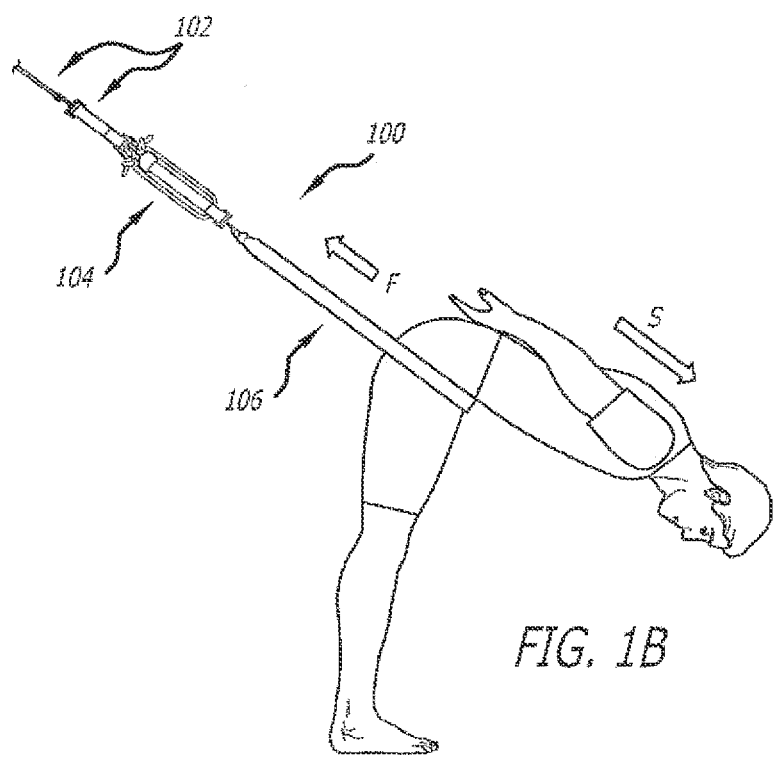

FIG. 1B shows the user 110 performing a forward bend using the body band 100. The body band 100 provides a supporting force F aligned with the body band 100, which supports the user's body as the user 110 leans forward. The supporting force F provides a fixed point for stretching the user's back muscles along stretch direction S as the user bends forward. As with the back bend shown in FIG. 1A, the user may adjust the angle of the supporting force F and stretch direction S relative to the floor by adjusting the length of the body band 100. The user may also select between a low, or substantially no, elasticity and a higher elasticity setting using the dual-tension band of the tension converter 104. By selecting the higher elasticity setting, the user 110 may add a sense of instability that induces supporting muscles to engage. The sense of instability created by the higher elasticity setting may also provide the user 110 with a more gradual transition to the fully extended forward bend. As with the back bend shown in FIG. 1A, the gradual transition may train the user's neuromuscular and neurological system to adjust to the fully extended pose by lessening the sense of vulnerability that the pose may induce. The user 110 may begin using the low elasticity setting and gradually move to the higher elasticity setting. The user's training in the forward bend provides the user with the benefits of stretching, including PNF stretching, and trains the user's muscles to more easily enter yoga poses requiring a deep forward bend and balance.

Figure 1C:
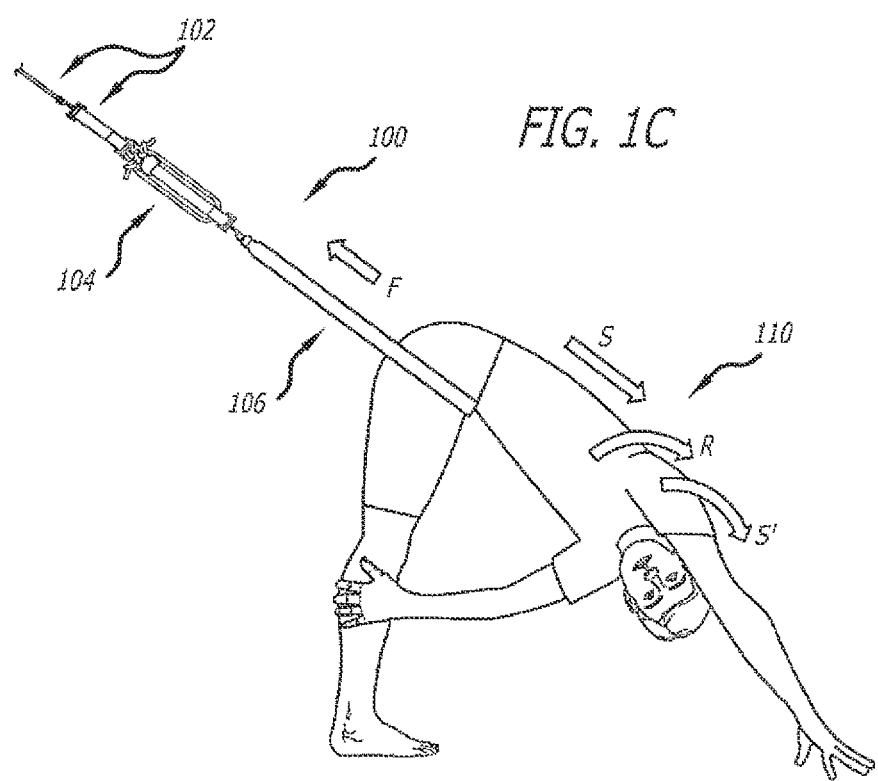

FIG. 1C shows the user 110 performing a forward bend using the body band 110 with an added rotation of the upper body. As described above with reference to FIG. 1B, the user 110 performs the forward bend to stretch the back along the stretch direction S against supporting force F. By twisting the upper body, the user 110 stretches upper body supporting muscles along a rotational stretch direction R. The user 110 may also deepen a stretch of the entire latissimus dorsi along second stretch direction S'. The user 110 may then repeat the stretches by twisting the upper body in the opposite direction. The user 110 may enhance the stretches by adding elasticity along the body band 100 as described above with reference to FIGS. 1A and 1B. The combination of stretches along the stretch directions S, S' and rotational stretch direction R increases the flexibility and strength of the user's muscles involved in rotational movement of the upper body about the hips. The supporting force F applied at the hips assists the user 110 in keeping the hips square during the rotational stretch.

Figure 1D:
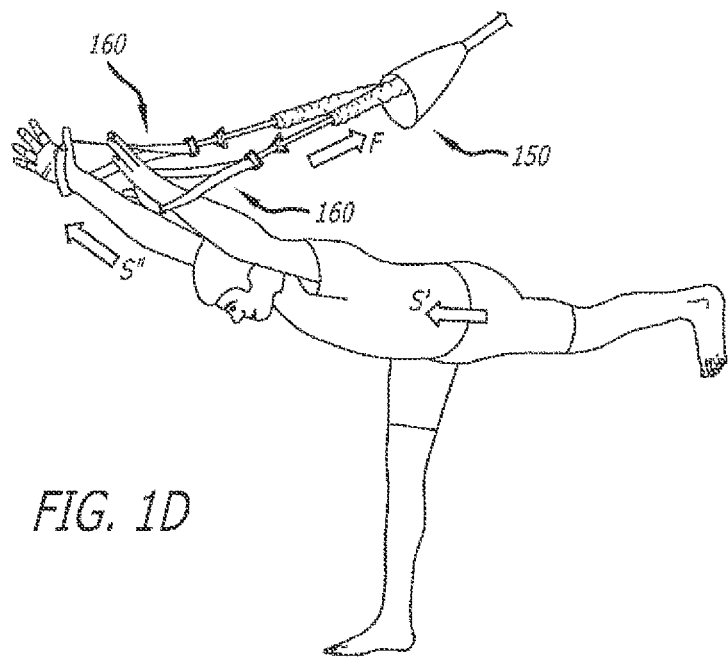

FIG. 1D shows the user 110 using an example of the body band that includes a second body band apparatus, which in FIG. 1D is an upper body band apparatus, or a dual-loop device 150. The dual-loop device 150 includes first and second hand loops 160 that may be connected to the attachment strap 102 shown in FIG. 1A. The hand loops 160 may connect to straps that connect at a point or at a destabilizing mechanism as described below with reference to FIGS. 4A to 4E.

The user 110 is shown using the upper dual-loop device 150 in a full body length stretch while balanced on one leg. The dual-loop device 150 provides points of support at the user's hands to generate a supporting force F along the dual-loop device 150. The supporting force F supports the user's efforts to stretch the extended leg along stretch direction S and to stretch the torso along stretch direction S'. The configuration of the dual-loop device 150 further permits the user 110 to stretch each arm along stretch directions S". The user's stretch along stretch directions S" acts cooperatively with the user's stretches along stretch directions S and S'. The cooperating action of the stretches along the three stretch directions while balanced on one leg inhibit the user 110 from applying an excessive force along any of the three stretch directions relative to the other directions. Therefore, the stretches along the three stretch directions are balanced relative to one another. In addition, the pose shown in FIG. 1D induces the user 110 into flexing muscles that enable the user to balance on one leg and muscles that produce the stretches in the three stretch directions. The pose implemented with the dual-loop device 150 on the body band assists the user 110 in making a mind-muscle connection that produces the balanced stretches and muscle contraction in a manner that simulates PNF stretching techniques. The dual-loop device 150 may provided further strength and flexibility benefits by allowing the user to include destabilization by adding elasticity in the straps that attach the two loops.

Figure 1E:
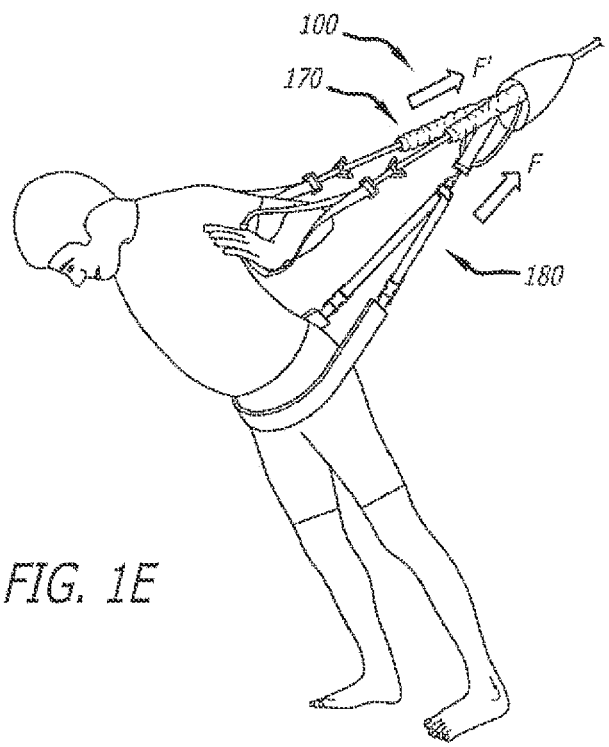

FIG. 1E shows the user 110 in a pose with an example of the body band 100 that includes an upper body band apparatus 170 and a lower body band apparatus 180. The upper body band apparatus 170 may be an example of the dual-loop device 150 shown in FIG. 1D. The lower body band apparatus 180 may be an example of the harness portion shown in FIG. 1A. By using both the upper and lower body band apparatuses 170, 180, the user 110 may further vary the stretch directions by combining supporting forces along force direction F and F'. The user 110 may add stretches of muscles in the user's core and throughout the user's upper body. The user 110 may increase the stretch and strengthening effects by adding destabilization using elasticity settings in either or both the upper body band apparatus 170 and the lower body band apparatus 180.

II. Components

Figure 2A:
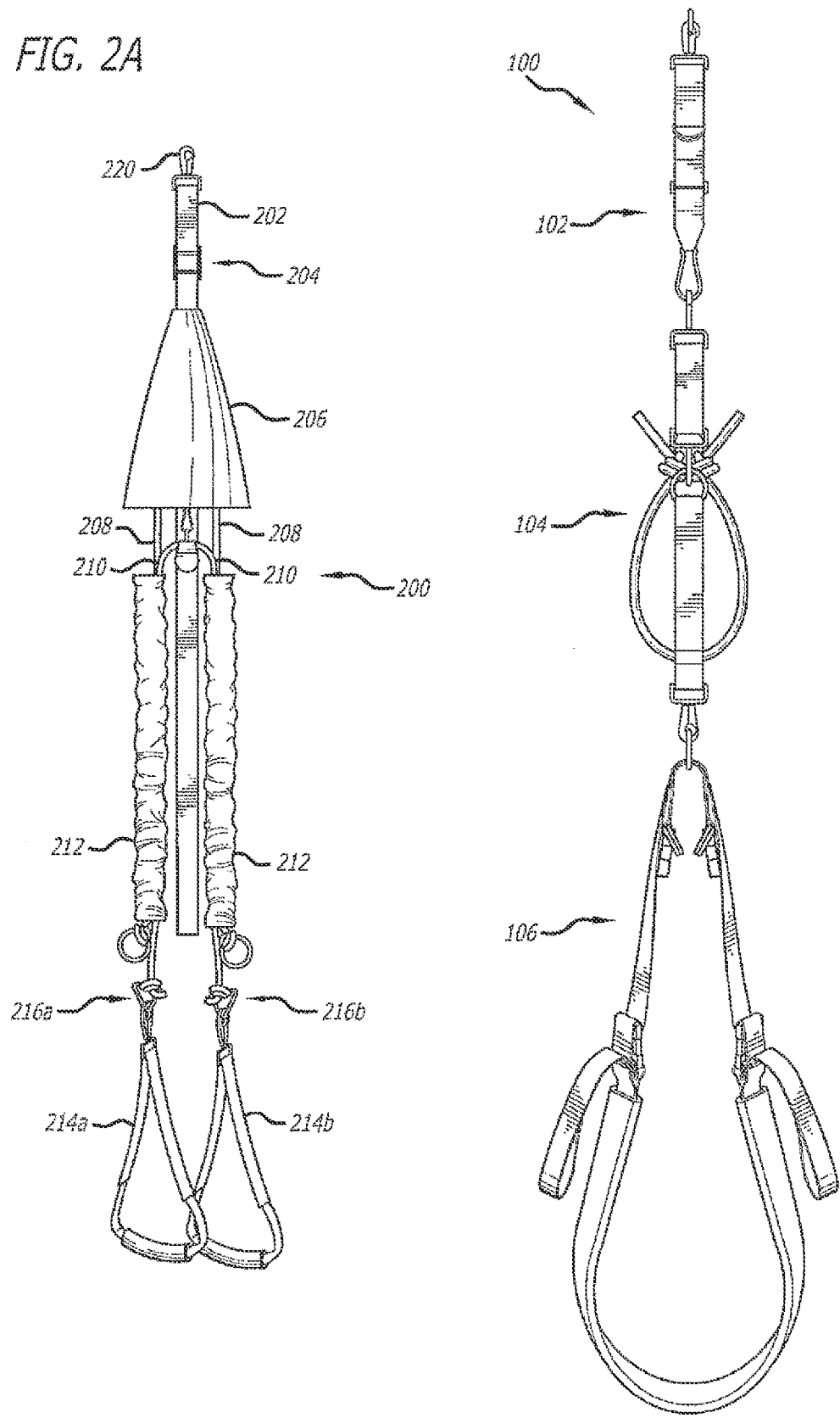
FIGS. 2A and 2B depict an example of a body band system that may be used in the applications in FIGS. 1A-1E.
Figure 2B:
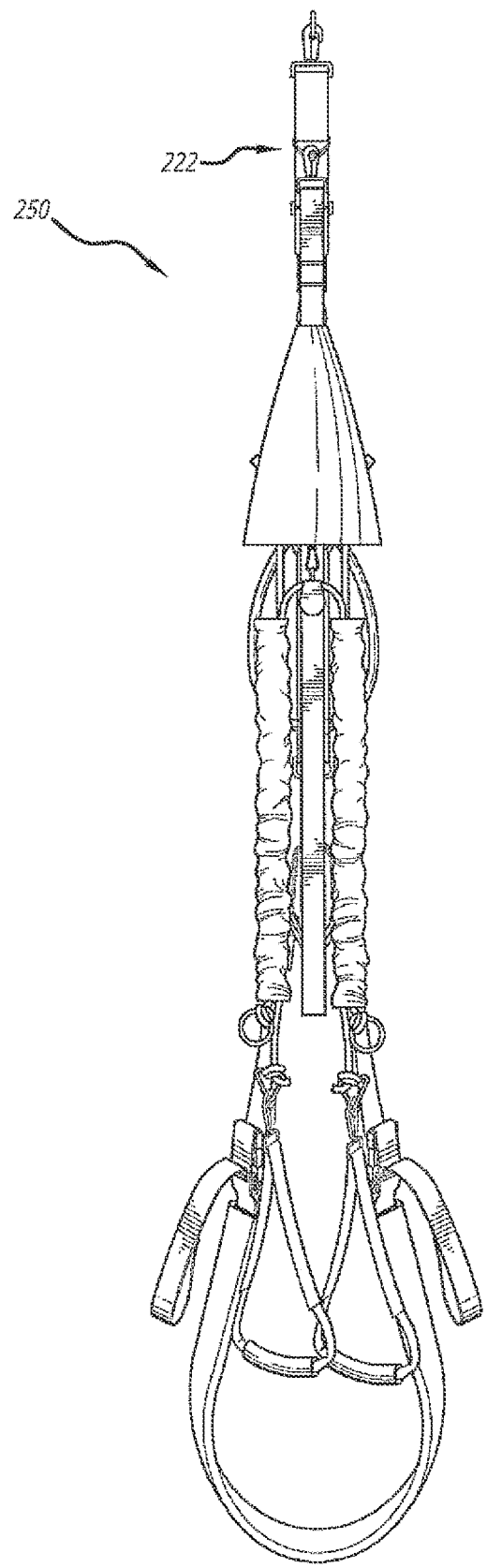

FIGS. 2A and 2B depict an example of a body band system that may be used in the applications in FIGS. 1A-1E. FIG. 2A shows the body band system 100 including the attachment strap 102, and a lower body band apparatus that includes the tension converter 104, and the harness portion 106. The lower body band apparatus is attached to the attachment strap 102. FIG. 2A also shows a dual-loop device 200, which is an example of an upper body band apparatus. It is noted that the terms "upper" and "lower" in reference to "upper" body band apparatus and "lower" body band apparatus refers to their relative attachment locations on the attachment strap 102, and are not intended to limit the application of either apparatus to any particular body portion.

The dual-loop device 200 in FIG. 2A includes an attaching segment 202, a dual-loop device length adjuster 204, a dual-loop joining mechanism 206, a first loop extension 208, a second loop extension 210, a pair of loop extension covers 212, a loop pair 214, a loop connection mechanism 216, and a dual-loop device attachment hook 220. The dual-loop device 200 attaches to the attachment strap 102 as described below, or directly to a wall or other structure. The dual-loop device 200 may be used in conjunction with the lower body band apparatus by attaching both to the attachment strap 102 as shown in FIG. 2B. FIG. 2B shows an example body band system 250 having the dual-loop device 200 attached to the attachment strap 102 at a connection point 222.

The attaching segment 202 on the dual-loop device 200 in FIG. 2A may include a segment of strap material with a hooking mechanism on one end and a strap adjuster or strap adjusting buckle on the other end. The hooking mechanism may be any suitable hook, such as a spring hook, a snap hook, a carabiner, or other similar hooks. A 'D' ring may be attached (by a bolt mechanism for example) to the hook for attaching one end of the strap material. The strap adjuster on the other end of the attaching segment 202 may be configured to attach to the dual-loop device length adjuster 204.

The dual-loop device length adjuster 204 may be any suitable strap adjuster configured to attach to the strap adjuster on the attaching segment 202. The dual-loop device length adjuster 204 holds a lengthening strap that attaches to the dual-loop joining mechanism on one end and extends through the dual-loop device length adjuster 204 to another end. The user may shorten the length of the dual-loop device 200 by pulling on the free end of the lengthening strap. The user may lengthen the dual-loop device 200 by activating a release on the dual-loop length adjuster 204 and allowing the lengthening strap to lengthen by the force of gravity, or by pulling on the lengthening strap in a lengthening direction. The dual-loop length adjuster 204 may include a clamp or other safety catch device to fix the length of the dual-loop device 200 while a pulling force is applied.

The dual-loop joining mechanism 206 is attached to the lengthening strap to move relative to the attaching segment 202 as the dual-loop device 200 is lengthened or shortened. The dual-loop joining mechanism 206 joins the first loop extensions 208 to form one pair of loops 214, which are used as supports for receiving forces applied by the user during exercise. The forces applied by the user are applied to extend the loop extensions 208, which provides a resistance during the exercise. The user may use the pair of loops 214 on each of a pair of limbs. It is noted that while the loops 214 in the examples shown in this specification are used by the user's hands, the loops 214 may be used for any pair of body parts including elbows, arms, shoulders, knees, ankles, feet, etc.

The dual-loop joining mechanism 206 optionally includes an attachment mechanism for a second loop extension 210 pair to provide alternative loop extensions for attaching the pair of loops 214. The optional second pair of loop extensions 210 may provide a more or less elastic extension, or a destabilizing mechanism, such as a pulley that challenges the user to apply balanced forces in order to maintain a balance.

It is noted that the dual-loop joining mechanism 206 in FIG. 2A is covered by a hood, which may be made of any suitable cloth, leather, suede, nylon or other material. The hood is used as a safety feature when the dual-loop joining mechanism 206 includes a pulley or other moving parts that may present a hazard during exercise. The loop extensions 208, 210 also include loop extension covers 212 as both a safety feature and as a conduit when more than one loop extension is used. The covers 212 may be made of any suitable cloth, leather, suede, nylon or other material. The hood and conduits may also be provided and designed for aesthetic purposes.

The loop pair 214 is connected to the first loop extension 208 or the second loop extension 210. The loop pair 214 may be any strap or length of material joined to form in a loop at a point that extends to attach to the loop connection mechanism 216. Each loop in the loop pair 214 may include a handle formed by a cylinder surrounding the strap material or by a padding with additional material along a length intended for gripping the loop. The loop connection mechanism 216 may attach to a length of material extending from each loop and may include any suitable hook. The loop connection mechanism 216 may attach to a ring or other suitable component at the end of each loop extension 208, 210.

The dual-loop device 200 may be used alone or in conjunction with the lower body band apparatus in the body band system 100. FIG. 2B shows the body band system 250 with both the dual-loop device 200 and the lower body band apparatus attached. The body band system 250 is shown hanging from a hook, eyelet, or other attachment mechanism on a wall. The body band system 250 may be fixed to a wall, or any other suitable structure such as a pole, ceiling, ceiling structure, or any other structure. In an example body band system application, the body band system 250 may be used in a body band studio having multiple systems 250 attached to one or more structures in a manner that facilitates group exercise.

The components of the body band system 250 and subsystems described above are described in more detail below with reference to FIGS. 3A-6B. It is noted that the components are described in the context of example implementations of the body band system 250 in FIG. 2B. Other example implementations may include more or fewer components that may also take other forms.

A. Attachment Strap

FIGS. 3A-3D depict an example attachment strap 300 that may be used in examples of a body band system. The attachment strap 300 attaches the body band apparatuses to the fixing structure, such as for example, a wall. The attachment strap 300 in FIG. 3A includes a first hooking device 302, a second hooking device 304, an adjusting slide 306, a lengthening strap 308 and a principle hook 312. The attachment strap 300 attaches to a wall by hooking the principle hook 312 to an eyelet 310 or other suitable mechanism mounted on a wall or other suitable structure. The principle hood 312 is attached at an attaching end of the attachment strap 300.

The first hooking device 302 may be one or more 'D' rings, 'O' rings, or other suitable structures configured to receive and hold a hook that is fixedly mounted in the attachment strap 300. The first hooking device 302 is configured in the illustrated examples to receive attachment of an upper body band apparatus. The second hooking device 304 is fixedly mounted at the extending end of the attachment strap 300 to receive attachment of the lower body band apparatus. It is noted that the terms "upper" and "lower" refer to the location of the attaching points of the corresponding apparatuses on the attachment strap 300 when both apparatuses are attached.

The adjusting slide 306 is positioned between the first and second hooking devices 302, 304 to permit adjustment of the length of strap between the two hooking devices 302, 304, and accordingly, between the attachment points of the upper and lower body band apparatuses. The length may be adjusted by pulling on the lengthening strap 308, which is shown in FIG. 3A in a folded state.

FIG. 3B shows the lengthening strap 308 unfolded and accessible to a user. The lengthening strap 308 may include a loop 314 at the end as a gripping option for the user. FIG. 3B shows the lengthening strap 308 slipped through the adjusting slide 306 and extending to the second hooding device 304. The length between the first hooking device 302 and second hooking device 304 may be shortened by pulling on the lengthening strap 308 and extended by activating a release on the adjusting slide 306 and pulling on the second hooking device 304. The release on the adjusting slide 306 may be accomplished by simply twisting the adjusting slide 306 to slacken the fold of the lengthening strap 308 through the slide 306 to allow the strap 308 to slip through the slide.

FIG. 3C shows the attachment strap 300 shows the dual-loop device 200 attached to the first hooking device 302 via the dual-loop device attachment hook 220. The first hooking device 302 includes two 'D' rings configured to receive the dual-loop device attachment hook 220. The second hooking device 306 is shown in FIG. 3C a relatively short distance away from the first hooking device 302. FIG. 3D shows the attachment strap 300 with a longer distance between the first hooking device 302 and the second hooking device 304. FIGS. 3C and 3D illustrate how the body band system 250 may be adjusted to accommodate different exercises and users of different sizes. The body band system 250 may also be adjusted for different affects during exercise by modifying the angles of resistance being applied to the body band system 250.

B. Dual-Loop Device

Figure 4A:
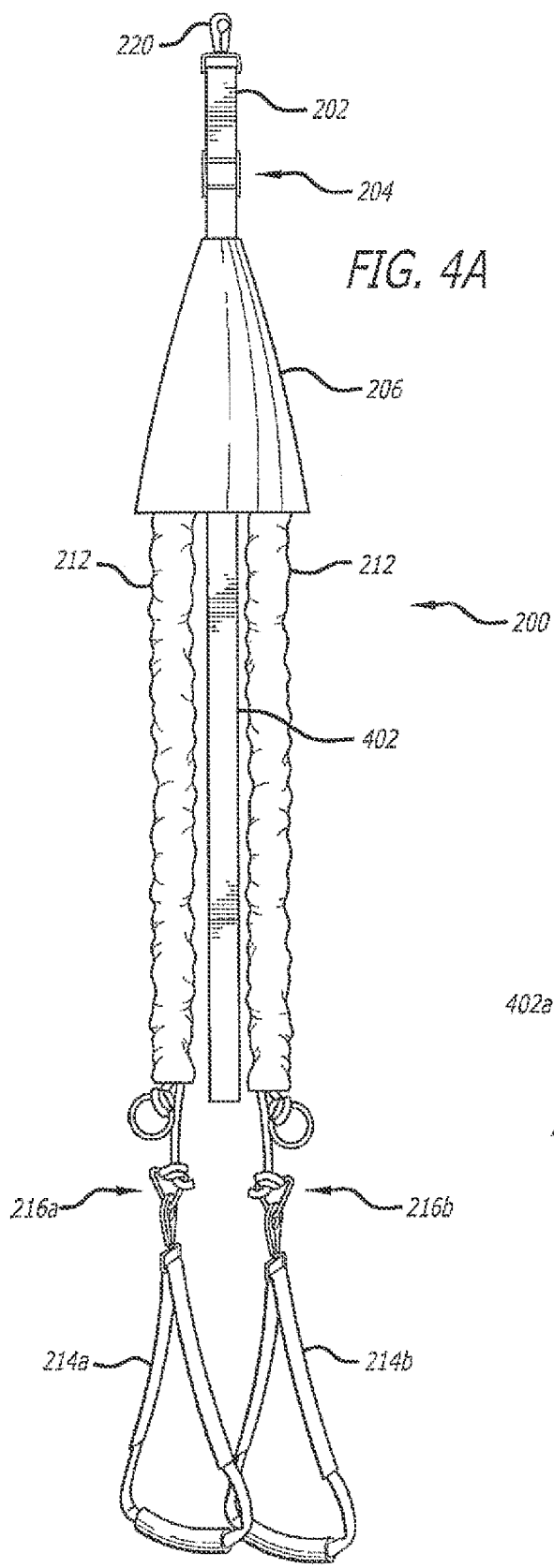

FIG. 4A-4F depict an example of a dual-loop band device 200 that may be used in examples of a body band system. FIG. 4A shows the dual-loop device 200 hanging from a wall by the dual-loop device attachment hook 220. The dual-loop device attachment hook 220 is fixedly mounted at one end of a strap 402, which slips through the dual-loop length adjuster 204. The strap extends through the dual-loop joining mechanism 206 to form the lengthening portion of the strap 402. FIG. 4A also shows the extension covers 212 on the extension pairs that connect to the first loop 214a on one end and the second loop 214b on the other end. The first and second handle loops 214a, 214b connect to the extensions pairs via first and second connection mechanisms 216a, 216b.

Figure 4B:
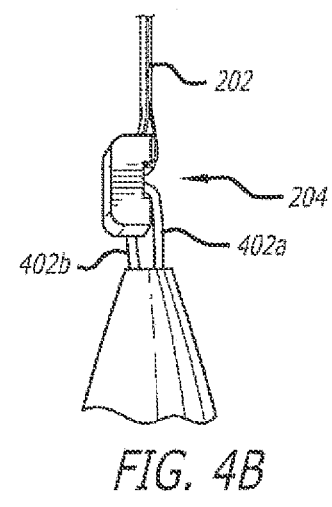

FIG. 4B shows a more detailed view of the dual-loop length adjuster 204. The dual-loop length adjuster 204 includes an adjusting slide and clamp. The strap 402 is slipped through the adjuster 204 to form a lengthening strap portion 402a on one side of the adjuster 204 and a supporting strap portion 402b on the other side of the adjuster 204. It is noted that any suitable length adjusting mechanism may be used for the dual-loop length adjuster 204.

Figure 4C:
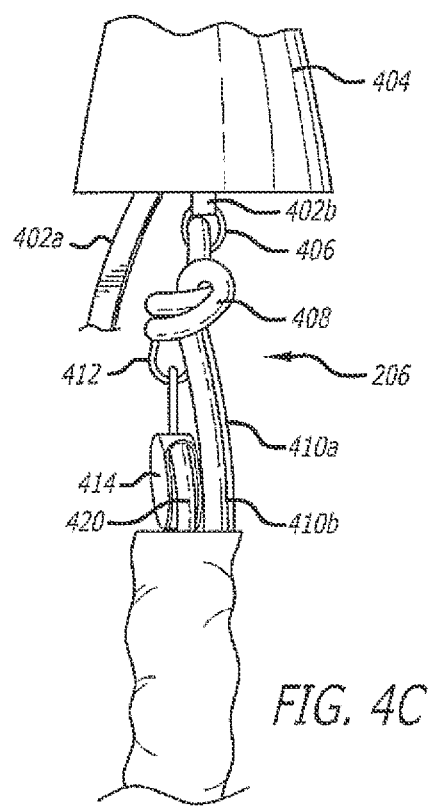
Figure 4D:
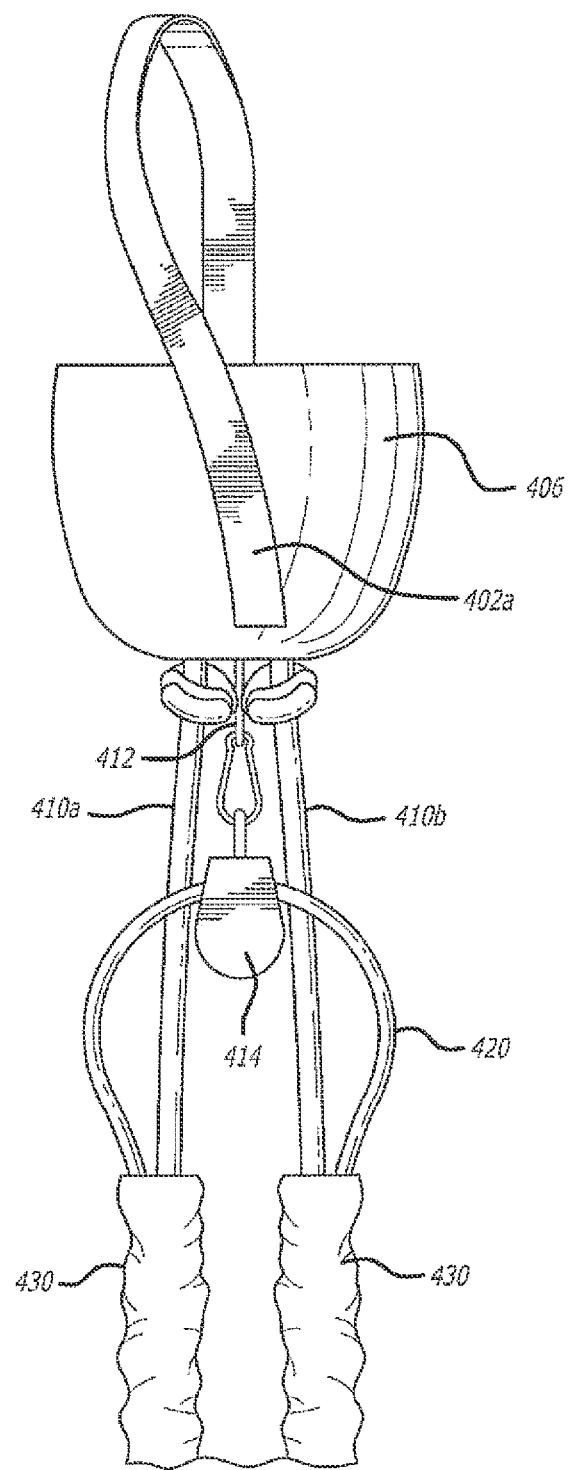

FIGS. 4C and 4D show the more detailed view of the dual-loop joining mechanism 206 with the hood 401 lifted to reveal its detail. FIG. 4C shows the detail from a side view while FIG. 4D shows the detail from a front view. The dual-loop joining mechanism 206 includes a strap bracket 406 attached to the supporting strap portion 402b. The strap bracket 406 in FIG. 4B is configured for attaching a first loop extension pair 410a, 410b, and a side destabilizing mechanism 414 having a second loop extension pair 420.

The first loop extension pair 410a, 410b may be implemented as a pair of bands that are tied to the strap bracket 406 in a band knot 408. The pair of bands is shown as either a single elastic rope knotted in the middle to allow the ends to extend as a pair of bands, or as two elastic ropes tied at the strap bracket 406. The first loop extension pair 410a, 410b forms a pair of force bearing lengths that may be elastic or substantially inelastic to provide resistance against the strap bracket 406. The elasticity may be selected to provide a degree of instability to challenge the user's balance along the direction of the supporting force.

The second loop extension pair 420 includes a strap or rope slipped through the destabilizing mechanism 414, which is a pulley in the example shown in FIG. 4C. The rope 420 may be elastic or substantially inelastic as desired and extends from the destabilizing mechanism 414 as a pair of rope lengths 420. The side destabilizing mechanism 414 attaches to a destabilizing mechanism hook 412, which is attached to the strap bracket 406, either directly, or via the knot 408. The side destabilizing mechanism hook 412 may be a spring hook or other suitable hook that allows the user to easily hook, or unhook the side destabilizing mechanism 414. The user unhooks the side destabilizing mechanism 414 to select use of the first loop extension pair 410a, 410b. The user hooks the side destabilizing mechanism 414 to select the second loop extension pair 420. The first and second loop extension pair 410a,b, and 420 extend to the loops in parallel. An extension cover 430 may be used as a conduit to keep the extension pairs cleanly together during operation.

Figure 4F:
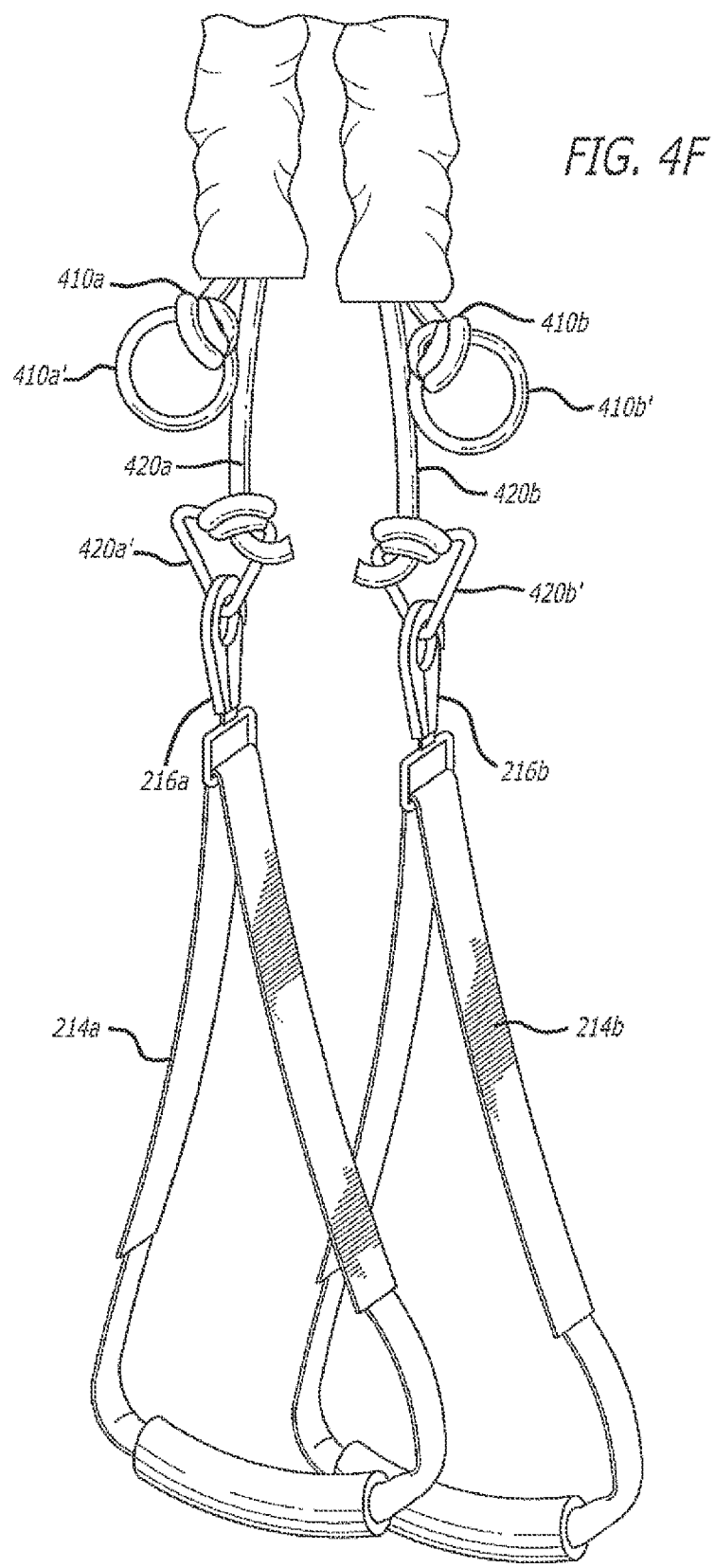

FIGS. 4E and 4F depict the first and second handle loops 214a, 214b, and the connection mechanisms for connecting the handle loops 214a, 214b to the extension pairs 410a, 410b, 420. FIG. 4A illustrates the first and second handle loops 214a, 214b having corresponding loop attachment hooks 216a, 216b. The loop attachment hooks 216a, 216b are hooked to corresponding extension pair hook receptacles 410a', 410b'. The extension pair hook receptacles 410a' and 410b' in FIG. 4E are 'O' rings attached to the ends of the first extension 410a, 410b. The first extensions 410a, 410b are attached with a knot around the 'O' rings. The configuration of the first and second handle loops 214a, 214b shown in FIG. 4E may be used when the side destabilizing mechanism 414 is unhooked from the strap bracket 406.

FIG. 4F illustrates the loop attachment hooks 216a, 216b of the corresponding first and second handle loops 214a, 214b hooked to a second pair of corresponding extension pair hook receptacles 420a', 420b'. The second pair of extension pair hook receptacles 420a' and 420b' in FIG. 4F are triangle rings attached to the ends of the second extension pair 420a, 420b. The second extensions 420a, 420b are attached with a knot around the triangle rings. The configuration of the first and second handle loops 214a, 214b shown in FIG. 4F may be used when the side destabilizing mechanism 414 is hooked to the strap bracket 406.

C. Tension Converter

FIGS. 5A and 5B depict an example of a tension converter 500 that may be used in examples of a body band system. The tension converter 500 provides the user with the option to switch between different tensions for the supporting force in the direction of the body band. In some exercises, a stiff tension may be desired or even required. Other exercises may be performed with a stretch in the band supporting the force applied along the band. The stretch may be provided to destabilize the body during particular exercises, or to allow the user to ease into a challenging position.

The tension converter 500 includes an attaching strap 502, a tension selector assembly 503, an elastic loop 510, a tension strap 512, a strap bracket 516, and an apparatus hook 518. The attaching strap 502 includes a hook 520 on one end for attachment to the body band attachment strap 102.

The plurality of tension lengths includes an elastic length and a less elastic length less elastic than the elastic length. An example of the elastic length is implemented in FIG. 5A as the elastic loop 510. An example of the less elastic than the elastic length is implemented in FIG. 5A as the tension strap 512.

The tension selector assembly 503 includes a bracket 504 on the other end of the attaching strap 502 connected to a hook and bolt 506. A ring 508, such as a 'D' ring or 'O' ring, may be fixed to the end of the strap near the bracket 504 for attaching first and second ends of the elastic loop 510a, 510b, which implement an example of the elastic length of the plurality of tension lengths. The elastic loop ends 510a, 510b in FIG. 5A are attached by a knot on the ring 508. The elastic loop 510 may extend from the ring 508 as a loop. The hook and bolt 506 extends between the two knots on the elastic loop ends 510a, 510b for hooking to a second ring 512' fixed to the end of the tension strap 512. The tension strap 512 implements an example of the less elastic length of the tension lengths, and includes a loop holding section 514, which may be an opening in the tension strap that holds an end of the elastic loop 510 opposite the tension selector assembly 503.

FIG. 5A shows the second ring 512' hooked to the hook and bolt 506 to affix the tension strap 512 to the force-bearing structure of the body band. The tension strap 512 hooked to the hook and bolt 506 bypasses the elastic loop 510 making the tension strap 512 an active force-bearing member during the use of the body band. FIG. 5B shows the second ring 512' unhooked from the hook and bolt 506. With the second ring 512' unhooked, the tension strap 512 is bypassed from the force-bearing structure of the body band. Instead, the elastic loop 510 receives the force applied during exercise between the tension selector assembly 503 where the elastic loop 510 and the loop holding section 514. The loop holding section 514 fixes the elastic loop 510 to the portion of the tension strap 512 that attaches to the strap bracket 516. The strap bracket 516 connects to the apparatus hook 518 for attaching the apparatus used to apply the force on the body band system. The elastic loop 510 may be generally more elastic than the elastic strap 512 to provide a stretch setting in which the tension converter 500 stretches when the force of the exercise is applied to the body band. The tension strap 512 is generally less elastic, or substantially inelastic, to provide a stiff resistance to the force applied to the body band.

D. Apparatus Portion

FIGS. 6A and 6B depict an example of a body band apparatus 600 that may be used in examples of a body band system. The body band apparatus 600 is the portion of the body band to which the user applies at least one force during an exercise. The body band apparatus 600 may include a harness portion 600 configured in a single loop as shown in FIG. 6A, or a double loop configuration 650 as shown in FIG. 6B.

The harness portion 600 in FIG. 6A may include a harness strap 602 and a hook receptacle 630. The hook receptacle 630 may be an 'O' ring, 'D' ring, or any other suitable hook receptacle adapted for hooking to the apparatus hook 518 on the tension converter 500 (in FIGS. 5A and 5B), or to an alternative strap, or directly to the attachment strap 300 (shown in FIG. 3A). The harness strap 602 includes first and second buckle portions 610a, 610b fixed on opposite sides of the hook receptacle 630 to a mini-strap 603. The mini-strap 603 may be attached to the harness strap 602 near the hook receptacle 630. A pair of 'D' rings 612 may be fixed to the mini-strap 603 near the buckle portions 610a, 610b to provide a tension lock using excess strap lengths.

The harness strap 602 may have first and second end buckle portions 606a, 606b fixed to opposite ends of the harness strap 602. The first and second end buckle portions 606a, 606b may be used with a single loop enabler to form a single loop harness configuration. In the example shown in FIG. 6B, the single loop enabler is implemented as a single loop harness extender 620, which includes a length of strap material having end buck portions 614a, 614b. The harness extender 620 connected to the harness strap 602 forms a single loop harness that may be fitted around the user's body or larger body parts in accordance with a desired exercise. The harness extender 620 may include a pad 604 for comfort when the single loop harness is fitted around the user. A pair of 'D' rings 612 may be attached to the harness extender strap 620 near the end buckle portions 614a, 614b. When the end buckle portions 606a, 606b are mated to the corresponding end buckle portions 614a, 614b on the harness extender strap 620, the user may adjust the fit by pulling the harness strap 602 at an excess strap portion 608. When the user has achieved a desired fit, the excess strap portion 608 may be slipped into the 'D' rings 612 near the end buckle portions 614a, 614b to lock the fit of the harness portion 600.

The double loop harness portion 650 may be formed by mating the end buckle portions 606a, 606b of the harness strap 602 to the first and second buckle portions 610a, 610b attached to the mini-strap 603. The double loop harness portion 650 forms first loop 650a and second loop 650b, which may be used to provide a rotational stretch on limbs fitted within the corresponding loops 650a, 650b. Applications that make advantageous use of a rotational stretch of body limbs are described in U.S. patent application Ser. No. 12/463,368 and U.S. patent application Ser. No. 12/695,708, both of which are incorporated by reference herein.

Figure 7A:
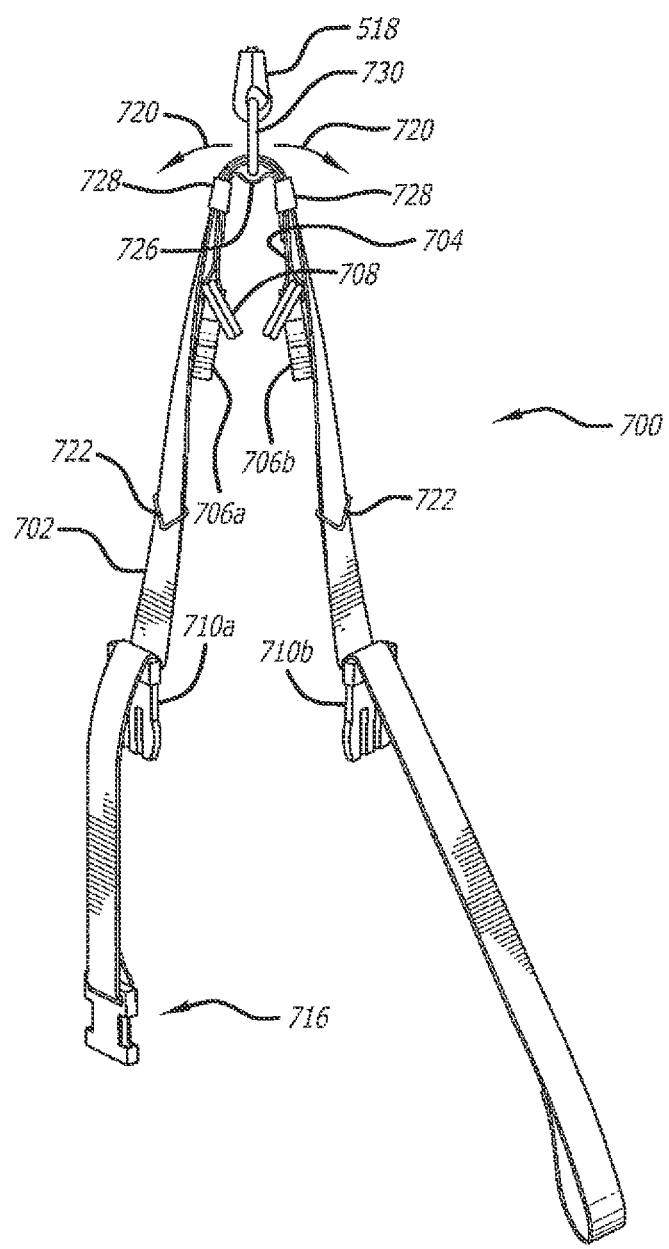

FIGS. 7A and 7B depict another example of a harness portion 700 that may be used in another example implementation of a body band system. The harness portion 700 in FIGS. 7A and 7B is similar to the harness portion in FIGS. 6A and 6B, except that the single loop configuration may be implemented using the harness portion 700 in FIG. 7A without the need to attach the single loop harness extender 620 shown in FIG. 6A. The harness portion 700 in FIG. 7A may also be configured to function as another example implementation of a dual-loop 750 similar to the dual-loop 200 described above with reference to FIG. 2A.

The harness portion 700 in FIG. 7A includes a harness strap 702 and a hook receptacle 730 similar to the hook receptacle 630 in FIG. 6A. The hook receptacle 730 may be an 'O' ring, 'D' ring, or any other suitable hook receptacle adapted for hooking to the apparatus hook 518 on the tension converter 500 (in FIGS. 5A and 5B), or to an alternative strap, or directly to the attachment strap 300 (shown in FIG. 3A). The harness portion 700 in FIG. 7 includes first and second buckle portions 706a, 706b fixed on opposite sides of the hook receptacle 630 to opposite ends of a mini-strap 704. The mini-strap 704 is positioned in the hook receptacle 630 and is attached to a pair of mini-strap sleeves 728 on opposite sides of the hook receptacle 730. A hook receptacle loop 726 formed by a strap material similar to the mini-strap is attached to the mini-strap 704 on opposite sides of the hook receptacle 630. The hook receptacle loop 726 is unattached from the mini-strap 704 in approximately the middle of the mini-strap 704 to form an opening. The hook receptacle 630 is inserted in the opening formed by the hook receptacle loop 726 to maintain the mini-strap 704 fixed in position relative to the hook receptacle 630. A pair of 'D' rings 708 may be fixed to the mini-strap 704 near the buckle portions 706a, 706b to provide a tension lock using excess strap lengths.

The harness strap 702 is slipped through the mini-strap sleeves 728 and through the hook receptacle 630 to maintain the freedom to move when pulled in either direction indicated by curved line 720. The harness strap 702 also includes first and second end buckle portions 710a, 710b fixed to opposite extensions of the harness strap 702. The first and second end buckle portions 710a, 710b may be mated to the first and second buckle portions 706a, 706b attached to the mini-strap 704 to configure the double loop harness portion 750 shown in FIG. 7B, which is similar to the double loop harness portion 650 in FIG. 6B.

The harness strap 702 includes an auxiliary buckle portion 716 on one of the extensions of the harness strap 702. The auxiliary buckle portion 716 is a single loop enabler, which operates by mating with the second buckle portion 710b to form a single loop harness portion similar to the single loop harness portion 600 shown in FIG. 6A except without the need for harness extender strap 620.

The harness portion 700 shown in FIG. 7A may be used to assemble a simplified body band system capable of substantially the same functions as the body band system 100 shown in FIG. 2A. The harness portion 700 may be configured in a single loop harness configuration as described above by mating the auxiliary buckle portion 716 to the second buckle portion 710b. The harness portion 700 in the single loop configuration may then be hooked to either the tension converter 500 (in FIG. 5A), which may be attached to the attachment strap 300 (FIG. 3A). The harness portion 700 in the single loop configuration may also be attached directly to the attachment strap 300. In the single loop configuration, the harness portion 700 may be used to perform exercises such as those illustrated in FIGS. 1A, 1B, and 1C. The harness portion 700 includes auxiliary hook receptacles 722 to which other devices may be attached. For example, a pair of handles similar to the loop pairs 214 in FIG. 4A may be attached to the auxiliary hook receptacles 722 to permit the user to perform exercises similar to the exercise shown in FIG. 1E.

The harness portion 700 may be configured in the double loop configuration 750 shown in FIG. 7B. The double loop configuration 750 may be used to perform a hip extender exercise by creating a rotational stretch on limbs fitted within corresponding loops 750a, 750b. The harness portion in the double loop configuration 750 may also be used to perform the exercise illustrated in FIG. 1D as well as similar exercises. A destabilizing effect is created by the freedom of movement in the harness strap 702 through the mini-strap sleeves 728 similar to the effect created by the destabilizing mechanism 206 (the pulley) shown in FIG. 2A. A pair of handles similar to the loop pairs 214 in FIG. 4A may be attached to the auxiliary hook receptacles 722 while in the double loop configuration 750.

It is noted that the above described components may be made of any material that is suitable for the purpose and function of the component. The components implemented as straps and ropes may be made of nylon, cotton, canvas, rubber, plastic, or any other suitable material. The material may be a type of material that is molded, weaved, extruded, or formed by some other means. The material may be made or selected to have a desired elasticity according to the intended function of the component as described above. The components implemented as buckles, slides, hooks and other hardware components may be made of plastic or any suitable metal with a strength and rigidity that is suitable for its intended purpose and function as described above.

It will be understood that the foregoing description of numerous implementations has been presented for purposes of illustration and description. It is not exhaustive and does not limit the claimed inventions to the precise forms disclosed. Modifications and variations are possible in light of the above description or may be acquired from practicing the invention. The claims and their equivalents define the scope of the invention.

What is claimed is:

1. A body band system comprising:
   a harness portion comprising a harness strap, and a hook receptacle configured to surround the harness strap to support the harness strap when the hook receptacle is suspended, the harness strap including:
      a mini-strap shorter than the harness strap, the mini-strap extending in parallel with the harness strap in a center harness strap portion to be enclosed by the hook receptacle with the harness strap, the mini-strap comprising first and second mini-strap buckle portions attached to each end of the mini-strap; and
      a first and second harness strap buckle portions movably attached on opposite extensions of the harness strap extending from the center harness strap portion, where the first and second harness strap buckle portions are configured to mate with the first and second mini-strap buckle portions to form a double loop harness configuration, and to combine with a single loop enabler to form a single loop harness configuration; and
   an attachment strap configured for attachment to a fixing structure at one end, the attachment strap comprising a movably attached hooking mechanism to vary the distance between the attaching end of the attachment strap and the hooking mechanism;
   where the harness portion is configured for attachment to the attachment strap attached to the fixing structure to provide a user with a body support while in un-balanced positions.

2. The body band system of claim 1 further comprising:
   a tension converter comprising:
      a first tension converter attachment mechanism for attaching to an attachment strap;
      a tension selector assembly comprising a plurality of tension lengths including an elastic length and a second length less elastic than the elastic length, the plurality of tension lengths configured to selectively attach at a first end to the first tension converter attachment mechanism; and
      a second tension converter attachment mechanism for attaching the tension converter to the harness portion where the plurality of tension lengths attach at a second end near the second tension converter attachment mechanism.

3. The body band system of claim 1 where the single loop enabler includes a harness extender having end buckle portions configured to mate with the first and second harness strap buckle portions to form a single loop.

4. The body band system of claim 1 where the harness portion is attached to the attachment strap at the movably attached hooking mechanism to implement a lower body band apparatus, further comprising:

an upper body band apparatus comprising a dual-loop band device attached to a second hooking mechanism on the attachment strap between the movably attached hooking mechanism and the end of the attachment strap that attaches to the fixing structure, the dual-loop band device comprising:
a dual-loop joining mechanism configured to attach the dual-loop band device to the attachment strap; and
an extension pair configured to connect to corresponding handle loops;
where the handle loops on the upper body band apparatus provides the user with upper body exercise variations.

5. The body band system of claim 4 where the extension pair is a first extension pair that is substantially elastic to provide resistance when pulled from the handle loops when attached to the dual-loop joining mechanism, the first extension pair being selectively detachable from the dual-loop joining mechanism, the dual-loop band device further comprising:
a second extension pair formed by a single strap less elastic than the first extension pair, the single strap disposed to move in the direction of the second extension pair depending on the direction of a pulling force applied to the second extension pair; and
a destabilizing mechanism configured to permit movement of the single strap forming the second extension pair, the destabilizing mechanism being selectively attachable to the dual-loop joining mechanism.

6. The body band system of claim 5 where the destabilizing mechanism includes a pulley or at least one sleeve.

7. The body band system of claim 1 where the mini-strap is fixedly attached to the harness strap in a mini-strap center portion enclosed by the hook receptacle.

8. The body band system of claim 1 where the harness strap further comprises an auxiliary buckle portion attached to an end portion of one of the extensions of the harness strap, the auxiliary buckle portion configured to mate with one of the harness strap buckle portions, where the auxiliary buckle portion is the single loop enabler configured to form a single loop when mated with one of the harness strap buckle portions.

9. The body band system of claim 1 where the mini-strap includes a hook receptacle loop to receive the hook receptacle and to fix the hook receptacle position to the center portion of the mini-strap, and two mini-strap sleeves fixedly attached to the mini-strap on opposite sides of the hook receptacle loop to permit the harness strap to slide through in friction contact with the mini-strap, where the mini-strap with hook receptacle loop and mini-strap sleeves operate as a destabilizing mechanism.

10. The body band system of claim 9 further comprising:
a first and second hooking mechanism movably disposed on corresponding extensions of the harness strap, where the first and second hooking mechanisms permit attachment of handle loops.

11. A body band system comprising:
a dual-loop band device comprising a dual-loop joining mechanism and a first and second extension pair extending from the dual-loop joining mechanism, the dual-loop band device configured to connect to corresponding handle loops, the first extension pair being substantially elastic to provide resistance when pulled from the handle loops when attached to the dual-loop joining mechanism, the first extension pair being selectively detachable from the dual-loop joining mechanism, the second extension pair formed by a single strap less elastic than the first extension pair, the single strap disposed to move in the direction of the second extension pair depending on the direction of a pulling force applied to the second extension pair;
a destabilizing mechanism configured to permit movement of the single strap forming the second extension pair, the destabilizing mechanism being selectively attachable to the dual-loop joining mechanism; and
an attachment strap configured for attachment to a fixing structure at one end, the attachment strap comprising a movably attached hooking mechanism to vary the distance between the attaching end of the attachment strap and the hooking mechanism;
where the dual-loop band attaches to the attachment strap at the dual-loop joining mechanism, and where the handle loops on the upper body band apparatus provides the user with upper body exercise variations.

12. The body band system of claim 11 where the destabilizing mechanism includes a pulley or at least one sleeve.

13. The body band system of claim 11 where the dual-loop band device is attached to the attachment strap to form an upper body band apparatus, further comprising:
a lower body band apparatus comprising a harness portion including a harness strap, and a hook receptacle configured to surround the harness strap to support the harness strap when the hook receptacle is suspended, the harness strap including:
a mini-strap shorter than the harness strap, the mini-strap extending in parallel with the harness strap in a center harness strap portion to be enclosed by the hook receptacle with the harness strap, the mini-strap comprising first and second mini-strap buckle portions attached to each end of the mini-strap; and
a first and second harness strap buckle portions movably attached on opposite extensions of the harness strap extending from the center harness strap portion, where the first and second harness strap buckle portions are configured to mate with the first and second mini-strap buckle portions to form a double loop harness configuration, and to combine with a single loop enabler to form a single loop harness configuration;
where the harness portion is configured for attachment to the attachment strap attached to the fixing structure to provide a user with a body support while in un-balanced positions.

14. The body band system of claim 13 further comprising:
a tension converter comprising:
a first tension converter attachment mechanism for attaching to an attachment strap;
a tension selector assembly comprising a plurality of tension lengths including an elastic length and a second length less elastic than the elastic length, the plurality of tension lengths configured to selectively attach at a first end to the first tension converter attachment mechanism; and
a second tension converter attachment mechanism for attaching the tension converter to the harness portion where the plurality of tension lengths attach at a second end near the second tension converter attachment mechanism.

15. The body band system of claim 13 where the single loop enabler includes a harness extender having end buckle portions configured to mate with the first and second harness strap buckle portions to form a single loop.

16. The body band system of claim 13 where the mini-strap is fixedly attached to the harness strap in a mini-strap center portion enclosed by the hook receptacle.

* * * * *